United States Patent
Barthelemy et al.

(10) Patent No.: US 11,116,437 B2
(45) Date of Patent: Sep. 14, 2021

(54) SCORING METHOD BASED ON IMPROVED SIGNALS ANALYSIS

(71) Applicant: CYREBRO TECHNOLOGIES, Paris (FR)

(72) Inventors: Quentin Barthelemy, Vanves (FR); Louis Mayaud, Paris (FR)

(73) Assignee: CYREBRO TECHNOLOGIES, Paris (FR)

( * ) Notice: Subject to any disclaimer, the term of this patent is extended or adjusted under 35 U.S.C. 154(b) by 681 days.

(21) Appl. No.: 15/526,351

(22) PCT Filed: Nov. 13, 2015

(86) PCT No.: PCT/EP2015/076629
§ 371 (c)(1),
(2) Date: May 12, 2017

(87) PCT Pub. No.: WO2016/075324
PCT Pub. Date: May 19, 2016

(65) Prior Publication Data
US 2017/0311832 A1 Nov. 2, 2017

(30) Foreign Application Priority Data
Nov. 13, 2014 (EP) .................................. 14193106

(51) Int. Cl.
| | |
|---|---|
| A61B 5/316 | (2021.01) |
| A61B 5/00 | (2006.01) |
| A61B 5/245 | (2021.01) |
| A61B 5/374 | (2021.01) |
| A61B 5/375 | (2021.01) |
| A61B 5/16 | (2006.01) |
| A61B 6/03 | (2006.01) |
| A61B 6/00 | (2006.01) |

(52) U.S. Cl.
CPC ............ *A61B 5/316* (2021.01); *A61B 5/0042* (2013.01); *A61B 5/0075* (2013.01); *A61B 5/165* (2013.01); *A61B 5/245* (2021.01); *A61B 5/374* (2021.01); *A61B 5/375* (2021.01); *A61B 5/4082* (2013.01); *A61B 5/4088* (2013.01); *A61B 5/7246* (2013.01); *A61B 5/7264* (2013.01); *A61B 6/037* (2013.01); *A61B 6/5217* (2013.01)

(58) Field of Classification Search
CPC . A61B 5/04014; A61B 5/0042; A61B 5/0075; A61B 5/04008; A61B 5/048; A61B 5/0482; A61B 5/165; A61B 5/4082; A61B 5/4088; A61B 5/7246; A61B 5/7264; A61B 6/037; A61B 6/5217
See application file for complete search history.

(56) References Cited

U.S. PATENT DOCUMENTS

| | | | | |
|---|---|---|---|---|
| 5,355,889 A | * | 10/1994 | Nevo .................. | A61B 5/0205 600/484 |
| 8,280,839 B2 | * | 10/2012 | Ivanov ................ | G06K 9/6252 706/54 |
| 2012/0071780 A1 | * | 3/2012 | Barachant .......... | A61B 5/04012 600/544 |
| 2013/0245394 A1 | | 9/2013 | Brown et al. | |
| 2014/0303424 A1 | * | 10/2014 | Glass .................... | A61N 2/006 600/9 |
| 2015/0119745 A1 | * | 4/2015 | Similowski ....... | A61M 16/0051 600/544 |

FOREIGN PATENT DOCUMENTS

| | | |
|---|---|---|
| WO | 2013164462 A1 | 11/2013 |
| WO | 2014107795 A1 | 7/2014 |

OTHER PUBLICATIONS

Subbarao et al. "Nonlinear Mean Shift over Riemannian Manifolds", Int J Comput Vis, 84. 2009. p. 1-20 (Year: 2009).*
Moakher, Maher. "A differential geometric approach to the geometric mean of symmetric positive-definite matrices", SIAM J. Matrix Anal. Appl. 26(3) 2005. p. 735-747 (Year: 2005).*
Congedo, Marco, "EEG Source Analysis", Neuroscience. Universite de Grenoble, 2013. p. 1-267 (Year: 2013).*
Stamoulis et al., "Space-Time Adaptive Processing for Improved Estimation of Preictal Seizure Activity," Conf Proc IEEE Eng Med Biol Soc, 2012. p. 1-11 (Year: 2012).*
Barachant, A., et al., "The Riemannian Potato: an automatic and adaptive artifact detection method for online experiments using Riemannian geometry," HAL. 2013, p. 1-3 (Year: 2013).*
Congedo, M., "EEG source analysis," HAL Neuroscience. 2013. p. 1-267 (Year: 2013).*
Barachant, A., Commande Robuste d'un Effecteur par une Interface Cerveau-Machine EEG Asynchrone, PhD. Thesis, Université de Grenoble: FR, 2012, 190 pages with English Abstract.
Förstner, W., et al., "A Metric for Covariance Matrices," Quo Vadis Geodesia, pp. 113-128, 1999.
Li, Y., et al., "Riemannian Distances for Signal Classification by Power Spectral Density," IEEE Journal of Selected Topics in Signal Processing, vol. 7, No. 4, Aug. 2013, pp. 655-669.
Subbarao, R., et al., "Nonlinear Mean Shift Over Riemannian Manifolds," Int. J. Comput. Vis, vol. 84, 2009, pp. 1-20.
Barachant, A., et al., "Multi-Class Brain Computer Interface Classification by Riemannian Geometry," IEEE Transactions on Biomedical Engineering, vol. 59, No. 4, 2012, pp. 920-928.

(Continued)

*Primary Examiner* — Michael J Tsai
*Assistant Examiner* — Sean A Frith
(74) *Attorney, Agent, or Firm* — Nixon & Vanderhye

(57) ABSTRACT

Disclosed is a method for scoring in real time neural signals of a subject with respect to a reference state characterized by k=1 . . . K reference covariance matrices, the method including the following steps: (i) obtaining neural signals from the subject; (ii) computing a covariance matrix of the neural signals; (iii) computing the Riemannian distances between the covariance matrix and k=1 . . . K reference covariance matrices; (iv) computing a continuous score s in real time based on at least one of the distances computed in step (iii). Also disclosed is a system and method for self-paced modulation or external modulation of neural activity of a subject.

20 Claims, No Drawings

(56) References Cited

OTHER PUBLICATIONS

Congedo, M. et al., "Habilitation Á Diriger des Recherche Presented to Doctoral School EDISCE," EEG Source Analysis, HDR, Université de Grenoble, Oct. 2013, 267 pages.
Fletcher, P.T., et al. "Principal Geodesic Analysis on Symmetric Spaces: Statistics of Diffusion Tensors," In Proceedings to Medical Image Analysis, Computer Vision and Mathematical Methods in Medical and Biomedical Image Analysis (CVAMIA), 2004, 12 pages.
European Search Report issued in Application No. EP14193106.3, dated May 13, 2015.
International Search Report issued in Application No. PCT/EP2015/076629, dated Feb. 1, 2016.
Jayasumana, S., et al., "Kernel Methods on the Riemannian Manifold of Symmetric Positive Definite Matrices," IEEE Conference on Computer Vision and Pattern Recognition, 2013, pp. 73-80.

\* cited by examiner

SCORING METHOD BASED ON IMPROVED SIGNALS ANALYSIS

FIELD OF INVENTION

The present invention relates to a scoring method, especially a method for scoring the neural activity of a subject based on neural signals analysis in a Riemannian manifold. In particular the present invention relates to a method for real time scoring of the neural signals of a subject with respect to a reference state. Said method may be used for external or self-paced modulation of the underlying brain activity.

BACKGROUND OF INVENTION

Ascertaining the position of the neural activity of a subject relative to a reference- or target-state in real time remains a challenge and presents many advantages. Said position relative to a reference state, estimated under the form of a score, may be subsequently used for self-paced modulation or external modulation. One of the key elements is the ability to reliably and robustly analyze and report the neural activity of a subject. In the present invention neural signals are characterized through descriptor named covariance matrix. Covariance matrices constitute good indicators of the subject's brain activity.

Said approach has already been used in Barachant et al. (US2012/0071780) and Similowski et al. (WO2013/164462).

However, to the best knowledge of the Applicant, there is no prior art on continuous scoring of the brain activity of a subject with respect to a reference state using covariance matrices in a Riemannian manifold.

Barachant discloses in US 2012/0071780 a classification method for classifying neural signals, the method comprising the following steps:
 a) using a plurality of electrodes over a determined period of time to acquire a plurality of neural signal samples;
 b) estimating a covariance matrix of said neural signals on non-overlapped window; and
 c) classifying said neural signals, the classification being performed: either in the Riemannian manifold of symmetric positive definite matrices of dimensions equal to the dimensions of said covariance matrix; or else in a tangent space of said Riemannian manifold.

Barachant describes two-class and multiclass classifications. In particular, Barachant discloses a method of classifying neural signals in a Riemannian manifold. The principle consists in defining, on the Riemannian manifold, so-called "class center" points, for example P1 and P2 corresponding to two distinct mental tasks: imagining moving a hand and imagining moving a foot. The Riemannian distance is calculated between the covariance matrix of a trial of cerebral activity that is to be classified and the corresponding class center point. If the Riemannian distance between a covariance matrix of a trial of cerebral activity and point P1 is less than the Riemannian distance between the covariance matrix of the trial of cerebral activity and point P2, then said trial of cerebral activity is associated with class No. 1 (moving the hand), otherwise it is associated with class No. 2 (moving the foot). Finally, classification step considers only the minimum of the distances to class centers.

Similowski discloses a method for characterizing the physiological state of a patient from the analysis of the cerebral electrical activity of said patient. In particular Similowski describes a method for detecting a physiological state of a patient deviating from a reference physiological state. Said method comprises first the determination of several reference matrices corresponding to a reference physiological state, and then the following steps are repeated in a loop:
 a) carrying out real-time measurements of an electroencephalographic signal and filtering the measurements in different frequency bands;
 b) for each frequency band, estimating a spatial covariance matrix of said measurements on a window/epoch;
 c) for each of the M last epochs, calculating the distance from the reference physiological states, defined as the sum over the frequency bands of the minimum distance between the current spatial covariance and the reference spatial covariance matrices;
 d) comparing each of the M distances to a predefined threshold. If one of the M distances is above the threshold, an abnormal physiological state is considered as detected.

Barachant et al. disclose a method for classifying neural signals by assign them to the class having the minimal distance, while Similowski et al. disclose a method for detecting a physiological state by comparing the distances between the neural signals and reference states to a predefined threshold. These two methods apply basic processing of the distances between covariance matrices, to finally obtain discrete values (class label for classification or binary state for detection).

One of the objects of the present invention is to report to a subject the position of its neural activity relative to a reference- or target-state in real time and optionally to enable said subject to modulate its neural activity towards said target state by self-paced modulation or external modulation.

To that end, the present invention provides a method for scoring neural signals of a subject with respect to a reference state, with the score defined as a transformation of the distance, ensuring continuous and bounded values between predetermined bounds.

On the contrary, the raw distances provided by Barachant et al. and Similowski et al. are meaningless to the subject.

The present invention provides a continuous feedback of the neural activity of the subject by reporting in real time the scoring of neural signals of the subject with respect to a reference state.

In contrast to Barachant et al., which classifies neural signals between at least two classes, and Similowski et al., which detects if a neural signals belong to a class or not (i.e. exceed the threshold); the present invention continuously and boundedly scores the neural signals with respect to a reference state, thereby continuously positioning the neural activity of a subject with regard to a single reference state.

The transformation of the distance into a score is made thanks to a non-linear function, with potential hyper-parameters which are adapted to the baseline state of the subject. It allows to have a score living in the complete range between two predetermined bounds, avoiding to always give a good score to a subject, or inversely, always a bad score.

Another point concerns the speed and the delay of processing. Barachant et al. wait the end of the trial (around 3s) to extract the covariance matrix and to apply its classification. As is, this framework cannot reach real-time processing. Similowski et al. use mobile windows of 4 to 12s to extract covariance matrices. Moreover, the detection step considers the last M matrices. If the processing is real-time, the length of windows and the number M of considered matrices are too high to have a real-time responsive system:

it gives a temporally smooth image of the brain activity, which is not suitable for neurofeedback. On the contrary to these approaches, the present invention extracts covariance matrices on overlapped windows, for example epochs of 1.5s all the 0.125s, thus actually capturing the current brain state.

SUMMARY

The present invention discloses an improved scoring method. In the present invention, the neural activity of a subject is analyzed in real time and the position of the neural activity with respect to a reference state is continuously and reliably reported to said subject by means of a bounded, continuous score. Said subject may in return modulating and modifying its neural activity and monitoring said evolution in real time in order to conduct its neural activity towards said reference state, either by self-paced modulation or external modulation.

The present invention relates in particular to a method for scoring in real time neural signals of a subject with respect to a reference state characterized by $k=1 \ldots K$ reference covariance matrices, the method comprising the following steps:
  i. obtaining neural signals from the subject;
  ii. computing a covariance matrix of said neural;
  iii. computing the Riemannian distances $d_k$ between said covariance matrix and $k=1 \ldots K$ reference covariance matrices;
  iv. computing a continuous score s in real time based on at least one of the distances $d_k$ computed in step iii.

According to one embodiment, the said score is bounded between two predetermined values a and b.

According to one embodiment, the present invention relates to a method for scoring in real time at least one neural signal of a subject with respect to a reference state characterized by $k=1 \ldots K$ reference covariance matrices, the method comprising the following steps:
  i. obtaining the at least one neural signal from the subject;
  ii. filtering the at least one signal in at least one frequency band; optionally, concatenating the at least one filtered signal;
  iii. computing a covariance matrix of said at least one filtered neural signal;
  iv. computing the Riemannian distances $d_k$ between said covariance matrix and $k=1 \ldots K$ reference covariance matrices;
  wherein the method further comprises the computing of a score s, said score s being continuous, computed in real time, bounded between two predetermined values a and b, and based on at least one of the distances $d_k$ computed in step iv.

According to one embodiment, the score is further based on at least one of the distances $d_r$ obtained as follows:
  obtaining $r=1 \ldots R$ baseline covariance matrices which are characteristic of a baseline state;
  computing the Riemannian distances $d_r$ between said $r=1 \ldots R$ baseline covariance matrices and the $k=1 \ldots K$ reference covariance matrices.

According to one embodiment, the score is based on at least one of the distances $d_k$, on the geometric means of the distances $d_r$ and on the geometric standard deviation of the distances $d_r$.

According to one embodiment, at least two neural signals are obtained, filtered in at least two frequency bands and concatenated.

According to one embodiment, the covariance matrix is a spatiofrequential covariance matrix.

According to one embodiment, the at least one neural signal is obtained by electrocorticography, electroencephalography, magnetoencephalography, magnetic resonance imaging, near-infrared spectroscopy, positron emission tomography or stereoelectroencephalography. According to one embodiment, the score s is continuous and bounded. According to one embodiment, step i also comprises preprocessing of said at least one neural signal, preferably by filtering. According to one embodiment, the covariance matrix is a spatiofrequential covariance matrix.

According to one embodiment, the Riemannian distances are estimated in the Riemannian manifold of symmetric positive definite matrices of dimensions equal to the dimensions of said covariance matrix.

According to one embodiment, the $k=1 \ldots K$ reference covariance matrices are obtained by a Riemannian clustering method from P covariance matrices of neural signals characteristics of the reference state from a database. According to one embodiment, the Riemannian clustering method is selected from mean-shift, k-means, average or principal geodesic analysis.

According to one embodiment, the $k=1 \ldots K$ reference covariance matrices are obtained by Mean-Shift as follows:
  i. obtaining $p=1 \ldots P$ covariance matrices $X_p$ of neural signals from a database and defining the initialization of Q=P modes, such as for $q=1 \ldots Q$, p=q and $M_q=X_p$;
  ii. defining the hyper-parameter h and the kernel window g;
  iii. for each mode $M_q$:
    a. computes the P distances $d(M_q, X_p)$ between $M_q$ and each matrix $X_p$;
    b. estimating the mean shift vector $m_h (M_q)$ as the weighted sum of tangent vectors $$m_h(M_q) = \frac{\sum_{p=1}^{P} g\left(\frac{d^2(M_q, X_p)}{h^2}\right) \mathrm{Log}_{M_q}(X_p)}{\sum_{p=1}^{P} g\left(\frac{d^2(M_q, X_p)}{h^2}\right)}$$

c. then, computes $M_q = \mathrm{Exp}_{M_q}(m_h(M_q))$, with $\mathrm{Exp}_{M_q}$ the exponential map with links a point on the tangent space to a point on the Riemannian manifold;
  d. while the mean shift vector $m_h (M_q)$ is superior to a threshold value repeat steps a. to c.;
  e. if the mean shift vector is inferior to a threshold value, retain $M_q$ as a local mode;
  iv. obtain K distinct local modes by fusion of modes with a distance inferior to h.

According to an alternative embodiment, the $k=1 \ldots K$ reference covariance matrices are obtained by k-means as follows:
  i. defining the hyper-parameter K;
  ii. obtaining $p=1 \ldots P$ covariance matrices $X_p$ of neural signals from a database and defining the initialization of the $k=1 \ldots K$ references $M_k$ (random or arbitrary attribution from the database);
  iii. for each matrix $X_p$:
    a. computing the K distances $d(M_k, X_p)$ between $X_p$ and each matrix $M_k$;

b. attributing matrix $X_p$ to the cluster $k_p$ giving the minimum distance $$k_p = \arg\min_{k=1\ldots K} d(M_k, X_p)$$

iv. updating the K reference matrices as the Riemannian means of the matrices attributed to their respective clusters:

v. $M_k$=Riemannian_Average $(\{X_p \text{ s.t. } k_p = k\}_{p=1}^P)$ vi. repeat steps iii and iv until the K reference matrices change no more from an iteration to another.

According to one embodiment, the k=1 . . . K reference covariance matrices further comprises at least one subject-specific covariance matrix.

The present invention also relates to a system for self-paced modulation or external modulation of neural activity of a subject comprising:
- acquisition means for acquiring at least one neural signal from a subject;
- computing device for implementing the method according to the present invention;
- output means for reporting the score s.

The present invention also relates to a method for self-paced modulation of neural activity of a subject in order to reach a reference state, said method comprising continuously:
- acquiring at least one neural signal from the subject; and
- reporting in real time to the subject a score s obtained by the method according to the present invention.

According to one embodiment, the said method for self-paced modulation is non-therapeutic.

The present invention also relates to a method for external modulation of neural activity of a subject in order to reach a reference state, said method comprising:
- acquiring at least one neural signal from the subject;
- reporting in real time to an operator a score s obtained by the method according to the present invention; and
- applying external modulation to the subject in order to modulate the score s towards a targeted score defined by the reference state.

According to one embodiment, the said method for external modulation is non-therapeutic.

According to one embodiment, the external modulation is applied by deep brain stimulation, electroconvulsive therapy, magnetic seizure therapy, transcranial direct current stimulation, transcranial magnetic stimulation, repetitive transcranial magnetic stimulation or vagus nerve stimulation. According to one embodiment, the external modulation also comprises indirect brain stimulation such as any sensory stimulation (auditory, visual, somatosensory).

Definitions

In the present invention, the following terms have the following meanings:

As used herein the singular forms "a", "an", and "the" include plural reference unless the context clearly dictates otherwise.

The term "about" is used herein to mean approximately, roughly, around, or in the region of. When the term "about" is used in conjunction with a numerical range, it modifies that range by extending the boundaries above and below the numerical values set forth. In general, the term "about" is used herein to modify a numerical value above and below the stated value by a variance of 20 percent, preferably of 5 percent.

"Baseline state" refers to a mental state of a subject, a population of subjects or a population of non-reference states which is not the reference state.

"Bounded": a score s is bounded, if the set of its value is bounded. In other words there exists a real number b such that $|s| \leq b$.

"Calibrated score" refers to a score s, which mean and standard deviation are set to desired values using a mathematical transformation wherein coefficients are derived from previously acquired data.

"Computing device" refers to a computer-based system or a processor-containing system or other system that can fetch and execute the instructions of a computer program.

"Discomfort" refers to the absence or to a decrease in the feeling of ease or well-being. In one embodiment, a discomfort may be related to the presence of pain.

"Disease, disorder or condition" refers to a defective state of health, wherein a physical or mental system is affected.

"Electrode" refers to a conductor used to establish electrical contact with a nonmetallic part of a circuit. For instance EEG electrodes are small metal discs usually made of stainless steel, tin, gold, silver covered with a silver chloride coating; there are placed on the scalp in specific positions.

"Electroencephalogram" or "EEG" refers to the tracing of brain waves, by recording the electrical activity of the brain from the scalp, made by an electroencephalograph.

"Electroencephalograph" refers to an apparatus for detecting and recording brain waves.

"Epoch" refers to a determined period during which neural signals are acquired.

"External or induced modulation" refers to the modulation of the brain activity which is not induced by the subject. Said modulation may comprise the following methods:
- Deep brain stimulation (DBS);
- Electroconvulsive therapy (ECT);
- Magnetic seizure therapy (MST);
- Transcranial direct current stimulation (tDCS);
- Transcranial magnetic stimulation (TMS);
- Repetitive transcranial magnetic stimulation (rTMS); or
- Vagus nerve stimulation (VNS).

External modulation also comprises any method of stimulation known by one skilled in the art which affect the brain's activity, e.g. drugs (sedation) or interventions (mechanical ventilation). Such stimulation may also indirectly affect the brain via sensory neural afferences: acoustic, visual, somatosensory stimulations. External modulation may also comprise simultaneous stimulation of elements of the two hemispheres of the brain at different frequencies of phase in order to elicit brain activity at frequency of interest in specific area of the brain (e.g. binaural beats for auditory stimulation).

"Neural signals" refers herein to the signals obtained by measuring neural activity. Said neural activity may be measured by:
- Deep brain electrodes;
- Electrocorticography (ECoG);
- Electroencephalography (EEG);
- Magnetoencephalography (MEG);
- Magnetic resonance imaging (MRI): diffusion MRI, perfusion MRI, functional MRI (fMRI);
- Near-infrared spectroscopy (NIRS);
- Positron emission tomography (PET); or
- Stereoelectroencephalography (SEEG).

The present invention refers to the acquisition and treatment of at least one neural signal or of neural signals "Real time" refers to a process for which the output is given within a time delay that is considered as smaller than the time delay required to perform the underlying task of modulation adequately. Therefore for self-paced modulation, real time refers to a process implemented in less than 700 ms, preferably less than 500 ms, more preferably less than 400 ms, even more preferably less than 250 ms. For external modulation real time may refer to a process implemented in less than 10 min, less than 1 min; less than 30s, less than is or less than 700 ms, depending on the frequency of the external modulation.

"Reference state" refers to the modeling of a cerebral state of a subject or a population of subjects carrying out a determined task, such as for example eyes-open resting, eyes-closed resting, relaxing, meditating, concentrating, focusing on a specific thought . . . .

"Riemannian manifold" refers to a differentiable topological space that is locally homeomorphic to a Euclidean space, and over which a scalar product is defined that is sufficiently regular. The scalar product makes it possible to define a Riemannian geometry on the Riemannian manifold.

"Score" refers to any value obtained or computed on a raw distance according to the present invention. In the sense of the present invention, the score is a bounded value which characterizes the position of the neural activity of a subject with respect to a reference state. The score is a value understandable to a subject, living on the complete range between two defined values.

"Self-paced modulation" refers to the modulation of the brain activity induced by the subject. In the sense of the present invention, self-paced modulation has the same meaning as neurofeedback and refers to the ability for the subject to control its brain electrical activity by manipulating in real time the score s. Self-paced modulation may include cognitive strategy such as predefined instructions given to the subject.

"Subject" refers to a mammal, preferably a human. In the sense of the present invention, a subject may be a patient, i.e. a person receiving medical attention, undergoing or having underwent a medical treatment, or monitored for the development of a disease.

"Symmetric positive definite (SPD) matrix" refers to a square matrix that is symmetrical about its diagonal (i.e. $A_{ij}=A_{ji}$,) and that has eigenvalues that are strictly positive. An SPD matrix of dimensions C*C has C(C+1)/2 independent elements; it may therefore be locally approximated by an Euclidian space of C(C+1)/2 dimensions. It is possible to show the SPD space has the structure of a Riemannian manifold. It is known that covariance matrices are symmetric positive definite matrices.

"Treating" or "treatment" or "alleviation" refers to both therapeutic treatment and prophylactic or preventative measures; wherein the object is to prevent or slow down (lessen) the targeted pathologic condition or disorder. Those in need of treatment include those already with the disorder as well as those prone to have the disorder or those in whom the disorder is to be prevented. A subject or mammal is successfully "treated" if, after receiving the treatment according to the methods of the present invention, the patient shows a lower score.

DETAILED DESCRIPTION

This invention relates to a method for scoring in real time neural signals of a subject with respect to a reference state characterized by k=1 . . . K reference covariance matrices, the method comprising the following steps:
i. obtaining neural signals from the subject;
ii. computing a covariance matrix of said neural signals;
iii. computing the Riemannian distances between the covariance matrix and k=1 . . . K reference matrices;
iv. computing a continuous score s based on the distances estimated in step iii.

According to one embodiment, the neural signals are acquired using magnetic resonance imaging (MRI), preferably fMRI, diffusion MRI or perfusion MRI. According to another embodiment, the neural signals are acquired using near-infrared spectroscopy (NIRS). According to one embodiment, the neural signals are acquired using magnetoencephalography (MEG). According to one embodiment, the neural signals are acquired using electrocorticography (ECoG). According to one embodiment, the neural signals are acquired using electroencephalography (EEG). In said embodiment, various types of suitable headsets or electrode systems are available for acquiring such neural signals. Examples includes, but are not limited to: Epoc headset commercially available from Emotiv, Mindset headset commercially available from Neurosky, Versus headset commercially available from SenseLabs, DSI 6 headset commercially available from Wearable sensing, Xpress system commercially available from BrainProducts, Mobita system commercially available from TMSi, Porti32 system commercially available from TMSi, ActiChamp system commercially available from BrainProducts and Geodesic system commercially available from EGI. According to one embodiment, the neural signals are acquired using positron emission tomography (PET). According to one embodiment, the neural signals are acquired using stereoelectroencephalography (SEEG). According to one embodiment, the neural signals are acquired using implanted microelectrod arrays. According to one embodiment, the neural signals are acquired using deep brain implants. According to one embodiment, the neural signals are acquired using any cerebral imaging technique known by one skilled in the art. According to one embodiment, the neural signals are acquired using a set of sensors and/or electrodes. According to one embodiment, the neural signals are acquired by at least 4, 8, 10, 15, 16, 17, 18, 19, 20, 25, 50, 75, 100, 150, 200, 250 electrodes.

According to one embodiment, the analyzed neural signals are raw neural signals or reconstructed neural signals. According to one embodiment, the analyzed neural signals are reconstructed from raw signals prior to analyze. According to one embodiment, the neural signals are obtained from reconstructed neural signals by any method known by one skilled in the art. According to one embodiment, the neural signals are acquired using positron emission tomography (PET). According to one embodiment, the signals are obtained using low resolution brain electromagnetic tomography (LORETA).

The overall acquisition time is subdivided into periods, known in the art as epochs. Each epoch is associated with a matrix $X \in \mathbb{R}^{C*N}$, representative of the spatiotemporal signals acquired during said epoch. A spatiotemporal neural signal $X \in \mathbb{R}^{C*N}$ is composed of C channels, electrodes or sensors and N time samples. For example, a subject is fitted with C electrodes for neural signals acquisitions. Each electrode c=1 ... C delivers a signal $X_c(n)$ as a function of time. The signal is sampled so as to operate in discrete time: $X(c, n)=X_c(n)$, and then digitized. This produced a matrix representation of the set of neural signals. According to one embodiment, in order to ensure real-time processing, successive epochs are overlapped.

According to one embodiment, the covariance matrix is a spatial covariance matrix. In an embodiment, the spatial covariance matrix may be computed as follows:

$$M = \frac{1}{N-1} X^T X,$$

with N≥C, where N is the number of samples in the epoch for each electrode and C the number of electrodes. In another embodiment, the spatial covariance matrix is computed using any method known by the skilled artisan, such as those disclosed in Barachant A. *Commande robuste d'un effecteur par une interface cerveau-machine EEG asynchrone*, PhD. Thesis, Université de Grenoble: FR, 2012.

According to one embodiment, the signal is pre-processed. According to one embodiment, the signal is centered. According to one embodiment, the signal is filtered. According to one embodiment, the signal is denoised. According to one embodiment, the signal is cleaned. According to one embodiment, the signal is frequency-filtered. According to one embodiment, the cut-off frequencies of the frequential filtering are chosen arbitrarily. According to another embodiment, the cut-off frequencies of the frequential filtering are optimized thanks to a preliminary frequential study.

According to one embodiment, the covariance matrix is normalized. According to one embodiment, the covariance matrix is trace-normalized, which makes its trace equal to 1:

$$M = \frac{M}{\text{trace}(M)}.$$

According to one embodiment, the covariance matrix is determinant-normalized, which makes its determinant equal to 1:

$$M = \frac{M}{\det(M)^{1/C}}.$$

The normalization step, especially the determinant normalization allows a session-to-session and/or a subject-to-subject transfer learning: it removes a part of variabilities from one recording to another.

According to one embodiment, the method of the invention scores in real time at least one neural signal. Said at least one neural signal is filtered in at least one frequency band. According to one embodiment, the method of the invention scores in real time at least two neural signals, filtered in at least two frequency bands. Said at least two filtered neural signals are further concatenated.

According to one embodiment, the signal $X \in \mathbb{R}^{C*N}$ is filtered in F frequency bands; thereby obtaining f=1 ... F filtered signals $X_f \in \mathbb{R}^{C*N}$. According to one embodiment, the extended signal $\tilde{X} \in \mathbb{R}^{CF*N}$ is defined as the vertical concatenation of the filtered signals:

$$\tilde{X} = \begin{bmatrix} X_1 \\ \vdots \\ X_f \\ \vdots \\ X_F \end{bmatrix}.$$

According to one embodiment, the covariance matrix is a spatiofrequential covariance matrix. In one embodiment, the spatiofrequential covariance matrix $\tilde{M} \in \mathbb{R}^{CF*CF}$ is computed as follows:

$$\tilde{M} = \frac{1}{N-1} \tilde{X}^T \tilde{X},$$

with N≥CF where N is the number of samples in the epoch for each electrode, and C the number of electrodes. According to one embodiment, the spatio-frequential covariance matrix can be normalized, as previously described, by its trace or its determinant.

According to one embodiment, the step of computing a covariance matrix of the neural signals comprises computing covariance matrix of said neural signals on overlapped window.

According to one embodiment, the step of computing a covariance matrix of the neural signals comprises computing a spatio-frequential covariance matrix of said neural signals on overlapped window, and normalizing said spatio-frequential covariance matrix.

Each covariance matrix associated with a given epoch is considered to be point of a Riemannian manifold. In order to position the neural activity of a subject relative to a reference population, distance and means calculation are required. The metric used for covariance matrices has been detailed in Förstner W, Moonen B. *A metric for covariance matrices*. Quo vadis geodesia, pp. 113-128, 1999.

In an embodiment, the Riemannian distance between two covariance matrices A and B may be defined as the affine-invariant distance:

$$d(A, B) = \left[ \sum_{i=1}^{n} \ln^2 \lambda_i(A, B) \right]^{\frac{1}{2}},$$

with $\lambda_i(A, B)$ the eigenvalues from $|\lambda A - B|=0$.

In another embodiment, the Riemannian distance is computed using any other distances known by one skilled in the art, such as those described in Li Y, Wong K M. *Riemannian Distances for Signal Classification by Power Spectral Density*. IEEE Journal of selected topics in signal processing, vol. 7, No. 4, August 2013.

According to one embodiment, the Riemannian distances are estimated on the Riemannian manifold of symmetric positive definite matrices of dimensions equal to the dimensions of the covariance matrices.

According to one embodiment, the Riemannian distances between the covariance matrix and k=1 ... K reference matrices are estimated.

According to one embodiment, the k=1 ... K reference covariance matrices are obtained by a Riemannian clustering method from P covariance matrices of neural signals from a database, with P≥K. Said P covariance matrices are characteristics of a reference state.

According to one embodiment, the P covariance matrices of the database are covariance matrices of neural signals characteristics of a reference state for different subjects and/or different sessions of neural signals acquisition.

According to one embodiment, the Riemannian clustering method is selected from Mean-shift, k-means, average or principal geodesic analysis.

According to one embodiment, Mean Shift over Riemannian manifold is performed.

According to one embodiment, Mean Shift over Riemannian manifold is performed as disclosed in Subbarao et al. *Nonlinear Mean Shift over Riemannian Manifolds*. Int J Comput Vis, vol. 84, pages 1-20 (2009).

According to one embodiment, the Mean Shift is performed iteratively.

According to one embodiment, the K reference covariance matrices (also called modes) are obtained by Mean-Shift as follows:
  i. obtaining $p=1 \ldots P$ covariance matrices $X_p$ of neural signals from a database and defining the initialization of Q=P modes, such as for $q=1 \ldots Q$, $p=q$ and $M_q=X_p$;
  ii. defining the hyper-parameter h and the kernel window g;
  iii. for each mode $M_q$:
    a. computes the P distances $d(M_q, X_p)$ between $M_q$ and each matrix $X_p$;
    b. estimating the mean shift vector $m_h(M_q)$ as the weighted sum of tangent vectors $$m_h(M_q) = \frac{\sum_{p=1}^{P} g\left(\frac{d^2(M_q, X_p)}{h^2}\right) \mathrm{Log}_{M_q}(X_p)}{\sum_{p=1}^{P} g\left(\frac{d^2(M_q, X_p)}{h^2}\right)}$$

c. then, computes $M_q = \mathrm{Exp}_{M_q}(m_h(M_q))$, with $\mathrm{Exp}_{M_q}$ the exponential map with links a point on the tangent space to a point on the Riemannian manifold;
  d. while the norm of the mean shift vector $m_h(M_q)$ is superior to a threshold value repeat steps a. to c.;
  e. if the mean shift vector is inferior to a threshold value, retain $M_q$ as a local mode;
  iv. obtain K distinct local modes by fusion of modes with a distance inferior to h;
wherein:

$$\mathrm{Exp}_A(B) = A^{\frac{1}{2}} \mathrm{expm}\left(A^{-\frac{1}{2}} B A^{-\frac{1}{2}}\right) A^{\frac{1}{2}}$$

$$\mathrm{Log}_A(B) = A^{\frac{1}{2}} \mathrm{logm}\left(A^{-\frac{1}{2}} B A^{-\frac{1}{2}}\right) A^{\frac{1}{2}}$$

with $\mathrm{Exp}_m$ and $\mathrm{Log}_m$ the exponential and logarithm functions for covariance matrices (see Barachant et al. *Multiclass Brain Computer Interface Classification by Riemannian Geometry*, IEEE Transactions on Biomedical Engineering 59, 4 (2012) 920-928 and Congedo M. *EEG Source Analysis*, HDR, Université de Grenoble: FR, 2013).

According to one embodiment, the threshold value is selected in order to ensure convergence of the algorithm and is preferably ranging from $10^{-1}$ to $10^{-3}$.

According to one embodiment, k-means over Riemannian manifold is performed.

According to one embodiment, k-means over Riemannian manifold is performed as disclosed in Congedo M. *EEG Source Analysis*, HDR, Université de Grenoble: FR, 2013.

According to one embodiment, the k-means is performed iteratively.

According to one embodiment, the K reference covariance matrices are obtained by K-means as follows:
  i. defining the hyper-parameter K;
  ii. obtaining $p=1 \ldots P$ covariance matrices $X_p$ of neural signals from a database and defining the initialization of the $k=1 \ldots K$ references $M_k$ (random or arbitrary attribution from the database);
  iii. for each matrix $X_p$:
    a. computing the K distances $d(M_k, X_p)$ between $X_p$ and each matrix $M_k$;
    b. attributing matrix $X_p$ to the cluster $k_p$ giving the minimum distance $$k_p = \arg\min_{k=1 \ldots K} d(M_k, X_p)$$

iv. updating the K reference matrices as the Riemannian means of the matrices attributed to their respective clusters:

$$M_k = \mathrm{Riemannian\_Average}(\{X_p s.t. k_p = k\}_{p=1}^{P})$$

v. repeat steps iii and iv until the K reference matrices change no more from an iteration to another.

The Riemannian Average is described in P. T. Fletcher and S. Joshi, "Principal geodesic analysis on symmetric spaces: Statistics of diffusion tensors," in Computer Vision and Mathematical Methods in Medical and Biomedical Image Analysis, 2004, pp. 87-98.

According to one embodiment, at least one supplemental reference covariance matrix is subject-specific. According to one embodiment, at least one supplemental reference covariance matrix is obtained by estimating the Riemannian means of the covariance matrices obtained from a calibration session of the subject. Said embodiment enables to provide a feedback that falls within acceptable and stimulating ranges of activity for the following session of the subject.

According to one embodiment, the $k=1 \ldots K$ reference covariance matrices are subject-specific. According to one embodiment, the $k=1 \ldots K$ reference covariance matrices are obtained by estimating the Riemannian means of the covariance matrices obtained from different session of the subject. Said embodiment enables to provide a feedback that falls within acceptable and stimulating ranges of activity for the following session of the subject.

According to one embodiment, a bounded, continuous score s based on the estimated distances $d_k$ between each covariance matrix and $k=1 \ldots K$ reference matrices is calculated. According to one embodiment, a bounded, continuous score s based on at least one of the estimated distances $d_k$ between each covariance matrix of and $k=1 \ldots K$ reference matrices is calculated. According to one embodiment, the score s is based on the smallest of the distances $d_k$ between each covariance matrix and the $k=1 \ldots K$ reference matrices.

According to one embodiment, the score is bounded between two predetermined values a and b.

According to one embodiment, the score s is further based on the estimated distances $d_r$ between covariance matrix of a baseline state and $k=1 \ldots K$ reference matrices.

Indeed, in order to be useful to a subject, the score must be bounded between two predetermined bounds. Moreover, in order to ensure that the score lies between the whole range of possible values, the transformation from the distance to the score need to be calibrated.

Thanks to the calibration, the score always lies in the complete range of potential values, thereby avoiding to give a quasi-constant score to a subject, for example, always a good score, or inversely, always a bad score. Said optimal use of the available range of score values strongly enhances neurofeedback efficiency.

According to one embodiment, the score s is calibrated. Calibration is the process of finding a relationship between an unknown quantity (a baseline activity of any subject at a given time) and a known quantity such as the operational range of a modulation device (for instance a voltage for a tDCS device, the volume of a speaker, or the lower and upper bounds of a display). The calibration process usually controls for the "bias" (the average departure from zero, or mean) and variance (the squared average departure from the mean/bias). Statistically speaking, the unknown quantity is usually characterized by a distribution (in the present case, distribution of Riemannian distances computed from a baseline session) that can be summarized by statistics such as the mean and standard deviation. The calibration procedure can therefore be expressed in terms of finding the mapping function transforming this baseline (uncontrolled) distribution into the operating range of a modulation device such as a current stimulator, a speaker, a screen, . . . In particular, it requires the target distribution to be bounded between two values. For improve treatment efficacy, it is also preferred that the final distribution makes optimal use of the available range of operating values. So that variance within those bounds is maximized.

According to said embodiment in order to calibrate the score, a database comprising r=1 . . . R baseline covariance matrices of neural signals corresponding to a baseline state, i.e. a non-reference or a non-target state, is used. Said database comprises neural signals obtained from different subjects and/or different sessions of neural signals acquisitions in a known baseline state. According to one embodiment, the database comprises covariance matrices of neural signals corresponding to a baseline state obtained from a previous session of neural signals acquisitions of the subject. Thus the score is calibrated in a subject-specific manner. According to another embodiment, the score s is calibrated in a subject-specific manner. Said embodiment enables to provide a feedback that falls within acceptable and stimulating ranges of activity for the following session of the subject.

According to one embodiment, the score s is also based on the estimated distances $d_r$ between each of the r=1 . . . R baseline covariance matrix and k=1 . . . K reference matrices. According to one embodiment, the score s is also based on at least one of the estimated distances $d_r$ between each of the r=1 . . . R baseline covariance matrix and k=1 . . . K reference matrices.

According to one embodiment, the score is based on at least one of the distances $d_k$, on the geometric means of the distances $d_r$ and on the geometric standard deviation of the distances $d_r$.

According to one embodiment, the Riemannian distance between the covariance matrix and k=1 . . . K reference matrices $d_k$ is transformed into a geometric z-score (standardized, i.e. unitary and zero-centered, normal distribution) using the following formula:

$$z(d_k) = \frac{\log(d_k / \mu)}{\log(\sigma)}$$

where the geometric mean μ and the the geometric standard deviation σ are computed on the r=1 . . . R baseline state distances $d_r$ as:

$$\mu = \exp\left(\frac{1}{R}\sum_{r=1}^{R} \log(d_r)\right)$$

and:

$$\sigma = \exp\left(\sqrt{\frac{1}{R}\sum_{r=1}^{R} (\log(d_r/\mu))^2}\right)$$

as disclosed in Congedo M. *EEG Source Analysis*, HDR, Université de Grenoble: FR, 2013.

According to one embodiment, the score s is estimated using a bounded function associating a score to a given standardized z-score. According to a preferred embodiment, said function belongs to the family of sigmoid functions. According to a preferred embodiment, said function is a logistic function, preferably:

$$s = a + \frac{b-a}{1 + \exp(-z(d_k))}$$

where a is the lower bound and b is the higher bound of the neurofeedback score.

According to one embodiment, said bounds a, b are predetermined (i.e. they are fixed as parameters).

According to one embodiment, the score s is strictly bounded between a and b wherein a is preferably equal to 0 and b is preferably equal to 10.

Another non-linear functions can be chosen to obtain a score from a z-score, such as generalized logistic function, hyperbolic tangent function, arctangent function, error function, and all other functions belonging to the family of sigmoid functions.

The transformation of the distance into a score is made thanks to a z-score standardization and then a non-linear function, which gives a score adapted to the relative state of the subject. It allows to have always a score living in the complete range of potential values, avoiding to give a quasi-constant score to a subject, for example, always a good score, or inversely, always a bad score. Capturing evolutions around to the relative state of the patient, the optimal use of the available range of score values is necessary for neurofeedback efficiency.

According to another embodiment, the score s is estimated using a logistic function, preferably:

$$s = 10 \times \frac{2}{1 + \exp(-\lambda \times d_k)} - 1,$$

where λ is a parameter chosen as detailed herebelow

According to said embodiment, a database comprising baseline covariance matrices of neural signals corresponding to a non-reference or non-target state is used. Said database comprises neural signals obtained from different subjects and/or different sessions of neural signals acquisitions in a known baseline state. The Riemannian distances between each of the covariance matrices of said database and the k=1 . . . K reference matrix obtained as detailed hereabove are estimated. The largest distance among said Riemannian distances is then referenced to as $d_{max}$. The parameter $\lambda$ can be chosen such that the sigmoid function associates to the distance $d_{max}$ a bounded score, preferably equal to 9.5. According to another embodiment, the score s is calibrated in a subject-specific manner. According to such embodiment, the database comprising covariance matrices of neural signals obtained from different subjects and/or different sessions of neural signals acquisitions in a known baseline state is replaced by covariance matrices obtained from a previous session of neural signals acquisitions of the subject. Said embodiment enables to provide a feedback that falls within acceptable and stimulating ranges of activity for the following session of the subject.

According to one embodiment, the score s is strictly bounded between a and b wherein a is preferably equal to 0 and b is preferably equal to 10.

According to one embodiment, the score s is not binary, coming from distances thresholding.

According to one embodiment, the score s is not a class label, coming from a multiclass classification.

In one embodiment, the present invention is implemented with a computer program stored on a computer-readable media for directing operation of a computing device. In one embodiment, the computer program comprises neural signal acquisition capabilities, preferably ECoG, EEG, MEG, MRI, NIRS, PET or SEEG acquisition capabilities. In another embodiment the computer program communicates with a system collecting neural signal data, preferably ECoG data, EEG data MEG data, MRI data, NIRS data, PET data or SEEG data.

The present invention also relates to a method for self-paced modulation of neural activity of a subject in order to reach a reference state, said method comprising continuously:
   acquiring neural signals from the subject; and
   reporting in real time to the subject a continuous score s obtained by the method according to the present invention.

By reporting in real time to the subject a score s, the subject is able to control the brain electrical activity such that the score s can be manipulated by the subject in real time.

According to one embodiment, instructions are given to the subject during the session of self-paced modulation; said instructions includes, but are not limited to, relax, breathe normally, remain quiet, avoid eye movement, avoid muscle tension, avoid sucking movements, avoid chewing, or avoid any movement.

According to one embodiment, no instructions are given to the subject during the session of self-paced modulation.

The present invention also relates a method for external modulation of neural activity of a subject in order to reach a reference state, said method comprising:
   acquiring neural signals from the subject;
   reporting in real time to an operator a score s obtained by the method according to the present invention;
   applying external modulation to the subject in order to modulate the score s towards a targeted score defined by the reference state. Preferably the external modulation is applied in order to minimize the score s.

According to one embodiment, the method for external modulation of neural activity of a subject in order to reach a reference state is not therapeutic.

According to one embodiment, the trainer may be a physician or an automated device applying the external modulation to the subject. According to one embodiment, the external modulation is applied by indirect brain stimulation, deep brain stimulation (DBS), electroconvulsive therapy (ECT), magnetic seizure therapy (MST), transcranial direct current stimulation (tDCS), transcranial magnetic stimulation (TMS), repetitive transcranial magnetic stimulation (rTMS) or Vagus nerve stimulation (VNS). According to one embodiment, the external modulation comprises indirect brain stimulation such as any sensory stimulation (auditory, visual, somatosensory).

The present invention also relates a system for self-paced modulation or external modulation of neural activity of a subject comprising:
   acquisition means for acquiring of neural signals from a subject;
   computing device for implementing the method according to the present invention;
   output means for reporting the score s.

According to one embodiment, the acquisition means comprises any means known by one skilled in the art enabling acquisition (i.e. capture, record and/or transmission) of neural signals as defined in the present invention, preferably electrodes or headset as explained hereabove. According to one embodiment, the acquisition means comprises an amplifier unit for magnifying and/or converting the neural signals from analog to digital format.

According to one embodiment, the computing device comprises a processor and a software program. The processor receives digitalized neural signals and processes the digitalized neural signals under the instructions of the software program to compute the score s. According to one embodiment, the computing device comprises memory. According to one embodiment, the computing device comprises a network connection enabling remote implementation of the method according to the present invention. According to one embodiment, neural signals are wirelessly communicated to the computing device. According to one embodiment, the output means wirelessly receives the score s from the computing device.

According to one embodiment, the output means comprise any means for reported the score s. According to one embodiment, the score s is reported using anyone of the senses of the subject: visual means, auditory means, olfactory means, tactile means (e.g. vibratory or haptic feedback) and/or gustatory means. Preferably the score s is reported using a display such as a screen: a smartphone, a computer monitor or a television; or a head-mounted display.

According to one embodiment, especially in the case of self-paced modulation, the reporting of the score s enables the subject to be aware of the right direction of the training. According to one embodiment, the reporting of the score s comprises a visual reporting wherein a target, representing the real-time score s of the subject, is displayed, said target moving towards or away from a location representing a target score defined by the reference state.

According to one embodiment wherein the score s is reported using auditory means, a sound, the amplitude of which is directly modulated by said score s, is reported to the subject. The sound can be a simple beep, water flowing, waves, rain, dongs, or any other sound which can be modulated in amplitude or frequency.

According to one embodiment wherein the score s is reported using visual means, an object on the screen, which position, size, color, or any other parameters can be modulated by said score s, is reported to the subject. For instance it can be the representation of a plane, the altitude of which is modulated by the score s.

According to one embodiment, the system and/or the method for self-paced modulation and/or external modulation is used in homecare or in clinical use.

The present invention also relates to the use of the system for self-paced modulation or external modulation for alleviating discomfort of a subject. According to one embodiment, the self-paced modulation method and/or the external modulation method is for alleviating, or for use in alleviating discomfort in a subject. The present invention also relates to a method for alleviating discomfort in a subject, comprising the use of the system for self-paced modulation or external modulation of the invention.

According to one embodiment, discomfort is psychiatric discomfort such as anxiety and stress.

According to one embodiment, the system and/or method for self-paced modulation and/or external modulation is used for alleviating chronic or acute pain, migraines and depression.

According to one embodiment, the system and/or the method for self-paced modulation and/or external modulation is used in order to reach the following target state: relaxation. According to this embodiment, the discomfort to be alleviated may be stress or anxiety.

The present invention also relates to the system for self-paced modulation or external modulation for treating or for use in treating a condition, a disorder or a disease such as those described hereafter in a subject, preferably in a patient in need thereof. According to one embodiment, the self-paced modulation method and/or the external modulation method is used for treating or alleviating conditions, disorders or diseases of patients. The present invention also relates to a method for treating a condition, disorder or disease in a subject in need thereof, comprising the use of the system for self-paced modulation or external modulation of the invention.

Examples of condition, disorder or disease that may be treated using the self-paced modulation method and/or the external modulation method of the invention include, but are not limited to neurodegenerative conditions, disorders or diseases, psychiatric conditions, diseases or disorders, primary insomnia, chronic or acute pain, epilepsy, Tourette's syndrome, migraines and depression.

According to one embodiment, said condition, disorder or disease to be treated is a neurodegenerative condition, disorder or disease, such as for example Parkinson's disease or Alzheimer's disease. According to one embodiment, the system and/or the method for self-paced modulation and/or external modulation enables treating Parkinson disease using surface and invasive EEG-based neuromarkers to reduce excess of beta activity. According to one embodiment, the system and/or method for self-paced modulation and/or external modulation enables treating Alzheimer's disease to reduce observed neuromarkers of Alzheimer's disease and increase brain fitness.

According to one embodiment, said condition, disorder or disease o be treated is a psychiatric condition, disease or disorder, such as for example attention-deficit/hyperactivity disorder, pervasive developmental disorder, autism, post-traumatic stress disorder, addiction and sleep disorder. According to one embodiment, the system and/or method for self-paced modulation and/or external modulation enables treating post-traumatic stress disorder by reducing the stress and amplification of inhibitory/filtering circuits for external stimuli. According to one embodiment, the system and/or method for self-paced modulation and/or external modulation enables treating attention deficit/hyperactivity disorder thanks to neuromodulation of concentration and the learning of cerebral pathways.

According to one embodiment, said condition, disorder or disease to be treated is selected from primary insomnia, chronic or acute pain, epilepsy, Tourette's syndrome, migraines and depression. According to one embodiment, the system and/or method for self-paced modulation and/or external modulation enables treating Primary insomnia thanks to the identification of the different stages preceding the onset of sleep and the dynamic feedback of said stages. According to one embodiment, the system and/or method for self-paced modulation and/or external modulation enables treating depression thanks to the reduction of depression neuromarkers and the balance of symmetrical EEG activity.

According to one embodiment, the system and/or method for self-paced modulation and/or external modulation is used for improving the sedation in intensive care unit, in operation theatre or in general ward. The present invention thus also relates to a method for improving the sedation in intensive care unit, in operation theatre or in general ward, comprising the use of the system and/or method for self-paced modulation and/or external modulation of the invention.

According to one embodiment, the system and/or method for self-paced modulation and/or external modulation is used for physical rehabilitation by activation and re-enforcement of pre-motor neural networks prior to trans-magnetic stimulation. The present invention also relates to a method of physical rehabilitation, comprising the use of the system and/or method for self-paced modulation and/or external modulation of the invention.

According to one embodiment, the system and/or method for self-paced modulation and/or external modulation is used for improving some of patient's specific cerebral activity meaning. The present invention thus also relates to a method for improving the specific cerebral activity meaning of a patient, comprising the use of the system and/or method for self-paced modulation and/or external modulation of the invention.

According to one embodiment, the system and/or the method for self-paced modulation and/or external modulation is used for improving skills of a subject, such as, for example, in healthy subjects (i.e. a subject that does not present any discomfort or disease, disorder or condition such as, for example, the ones listed hereinabove), such as precision.

The present invention thus also relates to methods for improving specific cerebral activity meaning, and/or for improving skills of a subject, comprising using the system and/or the method for self-paced modulation and/or external modulation of the invention.

In the view of the above detailed description, one skilled in the art could implement the method according to the present invention. Especially, the implementation of the method may use the following tools:
- a C++ template library for linear algebra such as that available on http://eigen.tuxfamily.org/index.php?title=Main_Page Retrieved Nov. 13, 2014;
- a set of functions dedicated to covariance matrices estimation and manipulation: (i) for Matlab such as that available on http://github.com/alexandrebarachant/covariancetoolbox Retrieved Nov. 13, 2014; (ii) for Python such as that available on http://github.com/alexandrebarachant/pyRiemann;
- a set of extensions for the OpenViBE platform, such as that available on http://code.google.com/p/openvibegipsa-extensions/ Retrieved Nov. 13, 2014. OpenViBE platform is a software for BCI (Brain Computer Interface) and real time neurosciences. It provides components for digital signal processing and visualization of EEG signal. It can be extended with modules in C++, Matlab and Python.

EXAMPLES

The present invention is further illustrated by the following examples.

Example 1

Validation of the System and Method for Self-Paced Modulation of the Neural Activity of a Subject The system and method for self-paced modulation (i.e. neurofeedback) proposed in the detailed description has been validated on real data. The target mental state was the relaxation, i.e. a state wherein the subject is free from tension and anxiety.

EEG data is composed of subject-specific sessions wherein each session is divided in two parts: relaxation and concentration. The purpose of the technique is to extract reference matrices on a training set (some EEG time-windows chosen randomly during the relaxation period), and to than apply these reference to test data (EEG time-window not included in the training set). The present method will be considered successful if the reference model accurately identifies relaxation period on the unseen data (i.e. the test set).

Materials and Methods

Recordings

The electroencephalography (EEG) data was collected using an Emotiv EPOC headset: the 14 electrodes were approximately located at the extended 10/20 locations AF3, F7, F3, FC5, T7, P7, O1, O2, P8, T8, FC6, F4, F8, AF4. The EPOC headset uses a Common Mode Sense (CMS) electrode at F4 location and a Driven Right Leg (DRL) electrode at F3 that can be related to the ground and reference in more traditional acquisition systems. Electrodes impedances were controlled visually with the EPOC Control Panel so that all sensors show "green". Signals are internally digitized at 2048 Hz (16-bit) and subsequently low pass filtered and down sampled to 128 Hz before transmission to the acquisition module. The headset was connected wirelessly to the participant laptop and interfaced with the NeuroRT Suite.

Data is composed of 61 sessions, divided in two parts by direction for the user displayed on the main screen:
i. 1 min of relaxation with eyes open; and
ii. 1 min of concentration with eyes open: to maintain an intense thought, subject counts back from 100, in intervals of 7.

Population

EEG data is acquired in Paris and Rennes (France), from 61 healthy participants aged between 23 and 34 years old.

Data Processing

The method we offer is quintessentially single class: we are trying to model one activity rather than trying to discriminate between two. Consequently, only the relaxation data was considered for training and for each relaxation session:
raw signal is filtered in 6 frequency bands (1-4-8-12-16-32 Hz);
spatio-frequential covariance matrices are extracted on overlapped epochs of 2s all 0.0625s and are regularized; and
the Riemannian average covariance matrix is computed on this relaxation part, called subject average matrix. This average matrix is then normalized, i.e. trace normalized or determinant-normalized.

At the end, one average matrix is obtained per participant totaling to 61 independent matrices.

Cross-Validation Procedure

A leave-one-out cross-validation procedure was used meaning that the 61 subject average matrices are divided in two sets: a training set composed of P=60 matrices, a test set composed of the single left-out matrix from which performance metric is derived as explained below. This procedure is repeated 61 times. The performance and its variation across all 61 tries are finally reported to allow for comparison between technique and the estimation statistical significance.

Data Clustering

The goal is to extract reference matrices on the training set by clustering, and to test them on the test set. The method according to the present invention will be considered successful if the test subject is closer from references during the relaxation part than during the concentration part.
1. A clustering algorithm (Riemannian average, Riemannian K-means, Riemannian Mean-Shift) is applied to estimate K reference matrices on the training set.
2. Considering the EEG session associated to the test matrix, spatio-frequential covariance matrices are extracted on epochs of the relaxation and concentration parts, as previously described, and normalized. The minimum distance between the K references matrices and each epoched covariance matrix is recorded.

Evaluation of Performances

For each test subject, the geometric mean of distances is computing for the relaxation and then for the concentration part. The neurofeedback is considered as efficient if the geometric mean of distances during relaxation is lower than the one during concentration. This evaluation is performed for the 61 test subjects.

Normalization

Two types of normalization have been tested for the covariance matrices: determinant and trace normalization for which results where compared.

Comparison with the State-of-the-Art

Traditional qEEG technique was considered as state-of-the-art and used to benchmark our technique as described below. The previous validation process is applied on same spectral powers. It is computed on overlapped epochs in all electrodes and in the 6 frequency bands chosen previously (1-4-8-12-16-32 Hz).

For each relaxation session, an averaged spectrum is computed, called subject average spectrum. In the leave-one-out process, the mean and standard deviation of subject average spectra of the training set are computed. Considering the EEG session associated to the test subject, spectra are extracted on epochs of the relaxation and concentration parts, as previously described. They are then transformed in z-score using the mean and the standard deviation estimated on the training set. The Frobenius norm of each z-scored spectrum is recorded as distance to relaxation qEEG model.

For each test subject, the mean of distances is computing for the relaxation and then for the concentration part. The neurofeedback is considered successful if the mean of distances during relaxation is lower than the one during concentration. This evaluation is performed using the exact same folds than previously described for the 61 subjects.

Results

The results of this validation framework are given below in percentage of successful sessions (i.e. the percentage of sessions having a means geodesic distance lower for the "relaxed" session than for the one where the subject is concentrated).

Regarding Table 1 and 2, determinant normalization gives better results than trace normalization. The normalization by the determinant seems provide a better discrimination between the two mental states. Moreover, k-means method appears to be the most efficient algorithm among the tested Riemannian clustering methods.

Regarding Table 3, results obtained by Riemannian clustering are superior to traditional qEEG; thereby validating the relevance and the efficiency of the method according to the present invention.

TABLE 1

Results with a trace normalization of matrices.

| Clustering method | Riemannian average | Riemannian k-means | Riemannian mean-shift |
|---|---|---|---|
| Performance in % | 63.9 | 67.2 | 62.2 |

TABLE 2

Results with a determinant normalization of matrices.

| Clustering method | Riemannian average | Riemannian k-means | Riemannian mean-shift |
|---|---|---|---|
| Performance in % | 67.2 | 70.5 | 62.2 |

TABLE 3

Results comparing traditional qEEG and Riemannian geometry.

| Approach | qEEG | Riemannian k-means |
|---|---|---|
| Performance in % | 59.02 | 70.5 |

Conclusion

This experiment validates the neurofeedback approach proposed in the present invention. According to the results, the Riemannian clustering offers a superior inter-subject generalization, since references matrices estimated on the training apply adequately to test data from different subject. Indeed, using the same input parameters, results obtained by Riemannian clustering are superior to traditional qEEG based neurofeedback, which we consider as the state-of-the-art for neurofeedback procedures. On average, the test subject is closer from references during the relaxation part than during the focus part. This paves the way for an efficient neurofeedback technique that does not require calibration.

Example 2

Self-Paced Modulation

In a population of subjects, a specific recording modality (ECoG, EEG, MEG, MRI NIRS or PET) allows the collection of data of neural signals. This data is analyzed to fit a model that defines a target activity (i.e. the reference state). In real time, the specific activity of a subject can be compared to the target according to the method of the present invention and the brain activity can be self-paced to reach the desired objective. The frequency and the length of sessions will vary for each application an on a case-by-case basis.

| Population | Modality | Target Activity | Modulation | Objective | Frequency/Length |
|---|---|---|---|---|---|
| Parkinson's patients | Surface EEG | Healthy EEG | Neurofeedback | Delay progression of Alzeihmer's disease | 1 h a day |
| ADHD patient | surface EEG | Concentration | Neurofeedback | Increase baseline concentration | 30 minutes every other day |
| Precision sportsmen (marksmen, archers, golfers) | Surface EEG | Pre-successful shots EEG | Neurofeedback | Increase movement precision | During practice |
| Primary insomnia | Surface EEG | Healthy EEG | Neurofeedback | Favor sleep | Daily (20 minutes) |

Example 3

External Modulation

In a population of subjects, a specific recording modality (ECoG, EEG, MEG, MRI NIRS or PET) allows the collection of data of neural signals. This data is analyzed to fit a model that defines a target activity. In real time, the specific activity of a subject can be compared to the target according to the method of the present invention and the brain activity can be externally modulated to reach the desired objective. The frequency and the length of sessions will vary for each application an on a case-by-case basis.

| Population | Modality | Target Activity | Modulation | Objective | Frequency/Length |
|---|---|---|---|---|---|
| Alzheimer's disease patients | Frontal EEG | Healthy EEG | Frontal tDCS | Delay progression of Alzeihmer's disease | 1 hour per day |
| Parkinson's patients | Deep EEG | Healthy reconstructed deep EEG | Beep Brain stimulation | Adjust stimulation to objective symptoms in order to save implant battery and delay progression of the disease | Continuous |
| Physical rehabilitation | Sensory-motor areas | Motor activation | Transcranial Brain Stimulation | Strengthen neural networks | 1 hour a day |
| Intensive Care Unit | Surface EEG | Absence of respiratory discomfort | Changes in mechanical ventilation setting | Optimize mechanical ventilation parameters and patients' comfort | Continuous (in the Intensive Care Unit) |
| Depression | Surface EEG | Healthy EEG | VNS | Adjust stimulation pattern to patient's status | Continuous |
| Apathic depression | Surface EEG | Healthy EEG | rTMS | Balance brain activity (left/right) and reduce symptoms | One a week |

We now present two applications using the described modeling technique. One application illustrates the use in a clinical context while the other concentrates on solution for the home.

Example 4

Detailed Example for ADHD (Attention Deficit Hyperactivity Disorder)

In the first place EEG data is collected from a population of healthy volunteers during a specific condition: eyes open, eyes closed, concentration or relaxation for instance. The collection of this reference dataset is done once and tries to cover equally the age ranges of interest for the application. The recording of each subject will last roughly 30 minutes and will use traditional EEG acquisition system such as those described hereabove, in particular Epoc commercially available from Emotiv.

Each 2s-long time window from this dataset will be converted into a covariance matrix and placed as a point in the Riemannian manifold. The artefactual periods will be identified iteratively. Then, the centers of reference (i.e. the k=1 . . . K reference covariance matrices) will be determined according to a Riemannian clustering method as described above.

ADHD children and teenagers are usually referred to medical and paramedical practitioners who handle comorbid conditions such as dyslexia. The treatment of ADHD is mostly composed of medication but recent evidence suggest that these patients exhibit different EEG patterns and neurofeedback protocols have therefore been implemented to correct these towards more normal electric activity of the brain. We offer to do so using a more accurate and intuitive feedback towards normal activity using the aforementioned reference state.

The patient arrives at the practitioner's clinic who setups the EEG data collection system. This can be done using clinical or research EEG system with 20 or more electrodes that require an individual setting. The whole setup procedure can take up to 20 minutes. Alternative EEG systems can also be used to reduce the setup time dramatically.

The application controls the signals and ensures that the data is collected adequately. In particular, a baseline recording makes sure that signals are not artefacted beyond acceptable limits. If so, feedback is provided to the operator in the form of auditory and visual instruction to indicate how to account for it. The operator decides of the length of the neurofeedback sessions and a type of feedback is chosen where the score s, obtained from the method according to the present invention can be represented by (non-exhaustive list):

a sound the amplitude of which is directly modulated by the score s, function of the Riemannian distances between the covariance matrix and k=1 . . . K reference covariance matrices; the sound can be a simple beep, water flowing, waves, rain, dongs, or any other sound which can be modulated in amplitude or frequency;

an object on the screen which position, size, color, or any other parameters can be modulated; for instance it can be the representation of a plane, the altitude of which is modulated by the score s, function of the Riemannian distances between the covariance matrix and k=1 ... K reference covariance matrices.

At the end of the session some early results are given to the practitioner and the patient: summary of the session, evolution between different sessions and comparison with the healthy population or a group of patients with similar patterns. The data is finally used to calibrate the model and provide a feedback that falls within acceptable and stimulating ranges of activity for the following session.

Example 5

Detailed Example for Primary Insomnia

A very similar procedure could be used at home for other medical conditions. Primary insomnia is a type of insomnia that could not be related to any organic origin. It was shown that population of patients with primary insomnia have increased beta activity in frontal areas prior to sleep. Consequently, this population is a good candidate for neurofeedback protocols, the true impact of which can only be seen for at-home applications.

Each session would happen shortly before bedtime on a voluntary basis or following a medical posology. The subject will use an easy-to-use general consumer EEG device that we will learn to setup on him. He logs on onto a secured website that connects to the EEG headset and retrieves his personal data and parameters. Data is streamed to a remote real time analysis server and extracted information is sent back to the web application, which for instance can display information to guide to subject to obtain good signal quality: for instance a real time 2 or 3D topographic heat map of signal quality. Figuring out good signals should take less than 5 minutes.

Once this is done, the subject can choose between several feedback applications that will work exactly like the applications described above. In real time his brain activity is compared to the previously identified reference covariance matrices and the computed distance to those is returned in the form of a feedback that can be visual or auditory (in a similar manner than what was described for ADHD in clinic). The patient can select the length of the session. At the end of the protocol, the web page stores and displays information related to performance, evolution of the score s and comparison to population and or other subjects.

The invention claimed is:

1. A system for self-paced modulation or external modulation of neural activity of a subject comprising:
   acquisition device for acquiring at least one neural signal from a subject;
   computing device programmed for:
      receiving the at least one neural signal from the subject acquired with said acquisition device;
      filtering the at least one neural signal in at least one frequency band;
      computing a covariance matrix of said at least one filtered neural signal;
      computing the Riemannian distances $d_k$ between said covariance matrix and k=1 ... K reference covariance matrices characteristic of a reference state; and
      computing a real time score s, based on at least one of the Riemannian distances $d_k$ and on at least one of Riemannian distances $d_r$, so as to be bounded between two predetermined values, wherein said Riemannian distances $d_r$ are obtained by:
         obtaining r=1 ... R baseline covariance matrices which are characteristic of a baseline state, said baseline state being different from the reference state; and
         computing the Riemannian distances $d_r$ between at least one of said baseline covariance matrices, for r=1 ... R, and the k=1 ... K reference covariance matrices;
   at least one modulation device configured to receive the score s and provide at least one output on the base of said score s to the subject so as to modulate and modify the neural activity of the subject towards the reference state.

2. The system according to claim 1, wherein the score s is based on a z-score function of the distances $d_k$ between the covariance matrix and the k=1 ... K reference covariance matrices, the geometric means of the distances $d_r$ and the geometric standard deviation of the distances $d_r$, for r=1 ... R.

3. The system according to claim 1, wherein the covariance matrix is a spatiofrequential covariance matrix.

4. The system according to claim 1, wherein the Riemannian distances are estimated in the Riemannian manifold of symmetric positive definite matrices of dimensions equal to the dimensions of said covariance matrix.

5. The system according to claim 1, wherein the k=1 ... K reference covariance matrices are obtained by mean-shift as follows:
   i. obtaining p=1 ... P covariance matrices $X_p$ of neural signals from a database and defining the initialization of Q=P modes, such as for q=1 ... Q, p=q and $M_q=X_p$;
   ii. defining the hyper-parameter h and the kernel window g;
   iii. for each mode $M_q$:
      a. computes the P distances $d(M_q, X_p)$ between $M_q$ and each matrix $X_p$;
      b. estimating the mean shift vector $m_h(M_q)$ as the weighted sum of tangent vectors $$m_h(M_q) = \frac{\sum_{p=1}^{P} g\left(\frac{d^2(M_q, X_p)}{h^2}\right) \text{Log}_{M_q}(X_p)}{\sum_{p=1}^{P} g\left(\frac{d^2(M_q, X_p)}{h^2}\right)}$$

c. then, computing $M_q = \text{Exp}_{M_q}(m_h(M_q))$, with $\text{Exp}_{M_q}$ the exponential map with links a point on the tangent space to a point on the Riemannian manifold;
      d. while the mean shift vector $m_h(M_q)$ is superior to a threshold value repeat steps a. to c.;
      e. if the mean shift vector is inferior to a threshold value, retain $M_q$ as a local mode;
   iv. obtain K distinct local modes by fusion of modes with a distance inferior to h.

6. The system according to claim 1, wherein the k=1 ... K reference covariance matrices are obtained by k-means as follows:
   i. defining the hyper-parameter K;
   ii. obtaining p=1 ... P covariance matrices $X_p$ of neural signals from a database and defining the initialization of the k=1 . . . K references $M_k$ (random or arbitrary attribution from the database);

iii. for each matrix $X_p$:
   a. computing the K distances $d(M_k, X_p)$ between $X_p$ and each matrix $M_k$;
   b. attributing matrix $X_p$ to the cluster $k_p$ giving the minimum distance $$k_p = \arg\min_{k=1\ldots K} d(M_k, X_p)$$

iv. updating the K reference matrices as the Riemannian means of the matrices attributed to their respective clusters:

$$M_k = \text{Riemannian\_Average}(\{X_p s.t. k_p = k\}_{p=1}^P)$$

v. repeat steps iii and iv until the K reference matrices change no more from an iteration to another.

7. A method for self-paced or external modulation of neural activity of a subject in order to reach a reference state, said method comprising continuously:
   acquiring at least one neural signal from the subject with an acquisition device; and
   in at least one computing device:
   filtering the at least one neural signal in at least one frequency band;
   computing a covariance matrix of said at least one filtered neural signal;
   computing the Riemannian distances $d_k$ between said covariance matrix and k=1 . . . K reference covariance matrices characteristic of the reference state; and
   computing a real time score s, based on at least one of the Riemannian distances $d_k$ and
   at least one of Riemannian distances $d_r$, so as to be bounded between two predetermined values, wherein said Riemannian distances $d_r$ are obtained by:
      obtaining r=1 . . . R baseline covariance matrices which are characteristic of a baseline state, said baseline state being different from the reference state, and
      computing the Riemannian distances $d_r$ between at least one of said baseline covariance matrices, for r=1 . . . R, and the k=1 . . . K reference covariance matrices;
and
   receiving in a modulation device the score s and provide in real time with said modulation device at least one output on the base of said score s to the subject so as to modulate and modify the neural activity of the subject towards the reference state.

8. The method according to claim 7, wherein said method further comprises applying external modulation to the subject in order to modulate the score s towards a targeted score defined by the reference state.

9. The method according to claim 8 wherein the external modulation is applied by deep brain stimulation, indirect brain stimulation, electroconvulsive therapy, magnetic seizure therapy, transcranial direct current stimulation, transcranial magnetic stimulation, repetitive transcranial magnetic stimulation or vagus nerve stimulation.

10. The method according to claim 7, wherein the at least one signal filtered in at least one frequency band is concatenated.

11. The method according to claim 7, wherein the score s is based on a z-score function of the distances $d_k$ between the covariance matrix and the k=1 . . . K reference covariance matrices, the geometric means of the distances $d_r$ and the geometric standard deviation of the distances $d_r$, for r=1 . . . R.

12. The method according to claim 7, wherein at least two neural signals are obtained, filtered in at least two frequency bands and concatenated.

13. The method according to claim 7, wherein the covariance matrix is a spatiofrequential covariance matrix.

14. The method according to claim 7, wherein the Riemannian distances are estimated in the Riemannian manifold of symmetric positive definite matrices of dimensions equal to the dimensions of said covariance matrix.

15. The method according to claim 7, wherein the k=1 . . . K reference covariance matrices are obtained by a Riemannian clustering method from P covariance matrices of neural signals characteristics of the reference state from a database.

16. The method according to claim 7, wherein the Riemannian clustering method is selected from mean-shift, k-means, average or principal geodesic analysis.

17. The method according to claim 7, wherein the k=1 . . . K reference covariance matrices are obtained by mean-shift as follows:
   i. obtaining p=1 . . . P covariance matrices $X_p$ of neural signals from a database and defining the initialization of Q=P modes, such as for q=1 . . . Q, p=q and $M_q = X_p$;
   ii. defining the hyper-parameter h and the kernel window g;
   iii. for each mode $M_q$:
      a. computes the P distances $d(M_q, X_p)$ between $M_q$ and each matrix $X_p$;
      b. estimating the mean shift vector $m_h(M_q)$ as the weighted sum of tangent vectors $$m_h(M_q) = \frac{\sum_{p=1}^{P} g\left(\frac{d^2(M_q, X_p)}{h^2}\right) \text{Log}_{M_q}(X_p)}{\sum_{p=1}^{P} g\left(\frac{d^2(M_q, X_p)}{h^2}\right)}$$

c. then, computing $M_q = \text{Exp}_{M_q}(m_h(M_q))$, with $\text{Exp}_{M_q}$ the exponential map with links a point on the tangent space to a point on the Riemannian manifold;
      d. while the mean shift vector $m_h(M_q)$ is superior to a threshold value repeat steps a. to c.;
      e. if the mean shift vector is inferior to a threshold value, retain $M_q$ as a local mode;
   iv. obtain K distinct local modes by fusion of modes with a distance inferior to h.

18. The method according to claim 7, wherein the k=1 . . . K reference covariance matrices are obtained by k-means as follows:
   i. defining the hyper-parameter K;
   ii. obtaining p=1 . . . P covariance matrices $X_p$ of neural signals from a database and defining the initialization of the k=1 . . . K references $M_k$ (random or arbitrary attribution from the database);
   iii. for each matrix $X_p$:
      a. computing the K distances $d(M_k, X_p)$ between $X_p$ and each matrix $M_k$;
      b. attributing matrix $X_p$ to the cluster $k_p$ giving the minimum distance $$k_p = \arg\min_{k=1\ldots K} d(M_k, X_p)$$

iv. updating the K reference matrices as the Riemannian means of the matrices attributed to their respective clusters:

$$M_k = \text{Riemannian\_Average}(\{X_p s.t. k_p = k\}_{p=1}^P)$$

v. repeat steps iii and iv until the K reference matrices change no more from an iteration to another.

19. The method according to claim 7, wherein the k=1 . . . K reference covariance matrices further comprises at least one subject-specific covariance matrix.

20. The method according to claim 7, wherein the at least one neural signal is obtained by electrocorticography, electroencephalography, magnetoencephalography, magnetic resonance imaging, near-infrared spectroscopy, positron emission tomography or stereoelectroencephalography.

* * * * *